(12) United States Patent
Blaney et al.

(10) Patent No.: US 6,663,611 B2
(45) Date of Patent: Dec. 16, 2003

(54) BREATHABLE DIAPER WITH LOW TO MODERATELY BREATHABLE INNER LAMINATE AND MORE BREATHABLE OUTER COVER

(75) Inventors: Carol Ann Blaney, Roswell, GA (US); Ann Louise McCormack, Cumming, GA (US); Christopher Dale Fenwick, Alpharetta, GA (US); Tamara Lee Mace, Doraville, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/407,587

(22) Filed: Sep. 28, 1999

(65) Prior Publication Data

US 2003/0163106 A1 Aug. 28, 2003

(51) Int. Cl.$^7$ .................................................. A61F 13/15
(52) U.S. Cl. ......................... 604/385.01; 604/385.101; 604/384; 604/385.23; 442/394; 442/398
(58) Field of Search ................................. 604/358, 362, 604/367, 375, 385.01, 385.101, 385.23, 385.12, 384; 424/98, 137, 172, 190; 442/327, 394, 398

(56) References Cited

U.S. PATENT DOCUMENTS 3,338,992 A    8/1967    Kinney ......................... 264/24
3,341,394 A    9/1967    Kinney ......................... 161/72

(List continued on next page.)

FOREIGN PATENT DOCUMENTS

| EP | 217 032 | 4/1987 | .......... D04H/13/00 |
| EP | 604 731 | 7/1994 | .......... B32B/31/00 |
| EP | 0 813 848 A1 | 12/1997 | .......... A61F/13/15 |

(List continued on next page.)

Primary Examiner—Weilun Lo
Assistant Examiner—Jacqueline F Stephens
(74) Attorney, Agent, or Firm—Pauley Petersen & Erickson (57) ABSTRACT

An absorbent article including a liquid-permeable top layer, an absorbent core layer, and a breathable outer cover is provided with a breathable inner laminate between the absorbent core and the outer cover. The breathable inner laminate includes a breathable film and a nonwoven filament web, and is less breathable than the outer cover. The low to moderately breathable inner laminate substantially reduces perceived dampness occurring on the external surface of the highly breathable outer cover, following a liquid insult, when the article is being worn, without seriously hampering moisture flux out of the diaper. Direct pathways for moisture near the wearer's skin to exit the article are maintained, and a concentration gradient is enhanced. Alternate embodiments include an apertured absorbent core, or the absence of a nonwoven filament web wherein the film and the absorbent core are apertured together, or a surge layer positioned between the top layer and the absorbent core wherein the surge layer extends to fill apertures in the absorbent core.

43 Claims, 4 Drawing Sheets

U.S. PATENT DOCUMENTS

| | | | |
|---|---|---|---|
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,695,269 A | 10/1972 | Malaney | 128/284 |
| 3,802,817 A | 4/1974 | Matsuki et al. | 425/66 |
| 3,849,241 A | 11/1974 | Butin et al. | 161/169 |
| 3,901,236 A | 8/1975 | Assarsson et al. | 128/284 |
| 3,949,128 A | 4/1976 | Ostermeier | 428/152 |
| 4,041,203 A | 8/1977 | Brock et al. | 428/157 |
| 4,076,663 A | 2/1978 | Masuda et al. | 260/17.4 GC |
| 4,196,245 A | 4/1980 | Kitson et al. | 428/198 |
| 4,223,677 A | 9/1980 | Anderson | |
| 4,282,874 A | 8/1981 | Mesek | 128/287 |
| 4,284,594 A | 8/1981 | Job et al. | 264/41 |
| 4,286,082 A | 8/1981 | Tsubakimoto et al. | 526/240 |
| 4,288,494 A | 9/1981 | Porter et al. | 428/398 |
| 4,306,559 A | 12/1981 | Nishizawa et al. | 128/287 |
| 4,308,303 A | 12/1981 | Mastroianni et al. | 428/90 |
| 4,340,563 A | 7/1982 | Appel et al. | 264/518 |
| 4,394,930 A | 7/1983 | Korpman | 220/444 |
| 4,663,220 A | 5/1987 | Wisneski et al. | 428/221 |
| 4,676,785 A * | 6/1987 | Battista | 604/369 |
| 4,681,793 A | 7/1987 | Linman et al. | 428/138 |
| 4,704,116 A | 11/1987 | Enloe | 604/385 A |
| 4,758,239 A | 7/1988 | Yeo et al. | 604/366 |
| 4,777,073 A * | 10/1988 | Sheth | 428/155 |
| 4,798,603 A | 1/1989 | Meyer et al. | |
| 4,818,600 A | 4/1989 | Braun et al. | 428/290 |
| 4,940,464 A | 7/1990 | Van Gompel et al. | 604/396 |
| 5,009,651 A | 4/1991 | Kamishioiri et al. | |
| 5,043,209 A | 8/1991 | Boissé et al. | 428/233 |
| 5,046,272 A | 9/1991 | Vogt et al. | 38/143 |
| 5,069,677 A | 12/1991 | Sakurai et al. | |
| 5,104,116 A | 4/1992 | Pohjola | 271/185 |
| 5,190,533 A * | 3/1993 | Blackburn | 604/367 |
| 5,224,405 A | 7/1993 | Pohjola | 83/24 |
| 5,226,992 A | 7/1993 | Morman | 156/62.4 |
| 5,264,268 A | 11/1993 | Luceri et al. | |
| 5,272,236 A | 12/1993 | Lai et al. | 526/348.5 |
| 5,294,478 A | 3/1994 | Wanek et al. | 428/218 |
| 5,300,054 A | 4/1994 | Feist et al. | 604/378 |
| 5,304,161 A | 4/1994 | Noel et al. | 604/378 |
| 5,306,266 A | 4/1994 | Freeland | |
| 5,322,728 A | 6/1994 | Davey et al. | 428/296 |
| 5,344,698 A | 9/1994 | Rock et al. | 428/253 |
| 5,346,487 A | 9/1994 | Lovestedt | 604/385.1 |
| 5,387,209 A | 2/1995 | Yamamoto et al. | 604/384 |
| 5,401,267 A | 3/1995 | Couture-Dorschner et al. | 604/384 |
| 5,439,458 A | 8/1995 | Noel et al. | 604/378 |
| 5,439,626 A | 8/1995 | Bennett et al. | 264/103 |
| 5,460,622 A | 10/1995 | Dragoo et al. | 604/378 |
| 5,466,513 A | 11/1995 | Wanek et al. | 428/218 |
| 5,505,719 A | 4/1996 | Cohen et al. | |
| 5,527,303 A | 6/1996 | Milby, Jr. et al. | 604/385.1 |
| 5,558,658 A | 9/1996 | Menard et al. | 604/385.1 |
| 5,569,226 A | 10/1996 | Cohen et al. | |
| 5,569,233 A | 10/1996 | Goulait | 604/391 |
| 5,571,096 A | 11/1996 | Dobrin et al. | 604/383 |
| 5,571,619 A | 11/1996 | McAlpin et al. | 428/364 |
| 5,591,297 A | 1/1997 | Ahr | 156/521 |
| 5,603,707 A | 2/1997 | Trombetta et al. | 604/383 |
| 5,626,571 A | 5/1997 | Young et al. | 604/370 |
| 5,643,239 A | 7/1997 | Bodford et al. | 604/370 |
| 5,653,699 A * | 8/1997 | Reed et al. | 604/307 |
| 5,656,372 A | 8/1997 | Gentile et al. | 428/376 |
| 5,658,639 A | 8/1997 | Curro et al. | |
| 5,680,653 A | 10/1997 | Mathis et al. | 2/123 |
| 5,695,868 A | 12/1997 | McCormack | 428/283 |
| 5,728,083 A | 3/1998 | Cohen et al. | |
| 5,752,945 A | 5/1998 | Mosley et al. | |
| 5,788,684 A * | 8/1998 | Abuto et al. | 604/368 |
| 5,792,404 A | 8/1998 | Cree et al. | |
| 5,810,797 A | 9/1998 | Menard et al. | 604/378 |
| 5,817,081 A | 10/1998 | LaVon et al. | 604/378 |
| 5,820,973 A | 10/1998 | Dodge, II et al. | |
| 5,843,055 A | 12/1998 | Seger | |
| 5,843,056 A | 12/1998 | Good et al. | 604/367 |
| 5,843,057 A | 12/1998 | McCormack | 128/849 |
| 5,843,064 A | 12/1998 | Koczab | |
| 5,843,066 A * | 12/1998 | Dobrin | 604/385.1 |
| 5,865,823 A | 2/1999 | Curro | 604/367 |
| 5,868,724 A | 2/1999 | Dierckes, Jr. et al. | |
| 5,876,388 A | 3/1999 | McDowall et al. | |
| 5,879,341 A * | 3/1999 | Odorzynski et al. | 604/367 |
| 5,897,541 A | 4/1999 | Uitenbroek et al. | 604/358 |
| 5,914,184 A | 6/1999 | Morman | 428/315.9 |
| 5,928,209 A | 7/1999 | Bodford et al. | 604/370 |
| 5,955,187 A | 9/1999 | McCormack et al. | 428/315.5 |
| 5,968,855 A | 10/1999 | Perdelwitz, Jr. et al. | |
| 5,989,688 A | 11/1999 | Barge et al. | |
| 5,990,377 A | 11/1999 | Chen et al. | 604/381 |
| 6,015,764 A | 1/2000 | McCormack et al. | 156/229 |
| 6,025,049 A | 2/2000 | Ouellette et al. | |
| 6,037,281 A | 3/2000 | Mathis et al. | 442/394 |
| 6,045,900 A * | 4/2000 | Haffner et al. | 428/315.9 |
| 6,072,005 A | 6/2000 | Kobylivker et al. | 525/240 |
| 6,075,179 A | 6/2000 | McCormack et al. | 428/131 |
| 6,096,014 A | 8/2000 | Haffner et al. | 264/41 |
| 6,103,954 A | 8/2000 | Grondin et al. | |
| 6,107,539 A | 8/2000 | Palumbo et al. | 604/358 |
| 6,152,906 A | 11/2000 | Faulks et al. | 604/385.01 |
| 6,177,607 B1 * | 1/2001 | Blaney et al. | 604/378 |
| 6,180,052 B1 | 1/2001 | Ouellette et al. | |
| 6,197,404 B1 | 3/2001 | Varona | 428/152 |
| 6,198,018 B1 | 3/2001 | Curro | 604/367 |
| 6,217,692 B1 | 4/2001 | Kling | 156/161 |
| 6,231,948 B1 | 5/2001 | Ouellette et al. | |
| 6,232,521 B1 | 5/2001 | Bewick-Sonntag et al. | |
| 6,238,379 B1 | 5/2001 | Keuhn, Jr. et al. | |
| 6,296,862 B1 | 10/2001 | Paul et al. | |
| 6,316,013 B1 | 11/2001 | Paul et al. | |
| 6,316,687 B1 | 11/2001 | Davis et al. | |
| 6,369,292 B1 * | 4/2002 | Strack et al. | 604/370 |
| 2002/0007171 A1 | 1/2002 | McMahon-Ayerst et al. | 604/385.14 |

FOREIGN PATENT DOCUMENTS

| | | | |
|---|---|---|---|
| EP | 0 893 113 A1 | 1/1999 | A61F/13/15 |
| EP | 1 051 958 | 11/2000 | |
| GB | 2029764 | 3/1980 | G32B/5/22 |
| GB | 2296216 | 6/1996 | B32B/27/12 |
| JP | 8164160 | 6/1996 | |
| JP | 2846448 | 1/1999 | |
| WO | 94/14394 | 7/1994 | |
| WO | 95/16422 | 6/1995 | |
| WO | 96/09165 | 3/1996 | B32B/27/12 |
| WO | 96/19346 | 6/1996 | B32B/7/00 |
| WO | 96/21409 | 7/1996 | A61F/13/00 |
| WO | 96/39109 | 12/1996 | A61F/13/15 |
| WO | 97/16148 | 5/1997 | A61F/13/15 |
| WO | 97/24095 | 7/1997 | A61F/13/15 |
| WO | 97/24097 | 7/1997 | A61F/13/15 |
| WO | 97/34557 | 9/1997 | A61F/13/15 |
| WO | 97/36561 | 10/1997 | A61F/13/15 |
| WO | 97/36562 | 10/1997 | A61F/13/15 |
| WO | WO 97/45259 | 12/1997 | |
| WO | 97/45259 | 12/1997 | B32B/27/12 |
| WO | 98/24621 | 6/1998 | |
| WO | 98/27920 | 7/1998 | A61F/13/15 |

| WO | 98/29480 | 7/1998 | ............... C08J/5/18 | WO | 99/32288 | 7/1999 | ............ B32B/27/12 |
| WO | 99/14047 | 3/1999 | ............ B32B/27/12 | WO | 99/55265 | 11/1999 | |
| WO | 99/16400 | 4/1999 | ............ A61F/13/15 | WO | 00/10497 | 3/2000 | ............ A61F/13/15 |
| WO | 99/22619 | 5/1999 | ............ A44B/18/00 | | | | |
| WO | 99/25283 | 5/1999 | ............ A61F/13/15 | * cited by examiner | | | |

BREATHABLE DIAPER WITH LOW TO MODERATELY BREATHABLE INNER LAMINATE AND MORE BREATHABLE OUTER COVER

FIELD OF THE INVENTION

The present invention is directed to an absorbent product having at least a top layer, an absorbent core, and a breathable outer cover material. A low to moderately breathable laminate, disposed between the absorbent core and the more breathable outer cover, reduces dampness on the outer surface of the breathable outer cover material without negatively increasing skin hydration of the wearer.

BACKGROUND OF THE INVENTION

Absorbent articles, such as diapers, child training pants, adult incontinence garments, swim wear and the like, typically include at least a liquid-permeable top layer for direct contact with the wearer, an absorbent core layer, and a substantially liquid-impermeable outer cover material. The absorbent core is positioned between the top layer and the outer cover material. When the absorbent article is exposed to a liquid insult, liquid passes through the top layer and into the absorbent core. The outer cover prevents the liquid in the absorbent core from leaving the garment.

Many of today's absorbent garments utilize breathable outer cover materials. Breathable outer cover materials are substantially impermeable to liquids, but are permeable to water vapor. Breathable outer cover materials permit escape of water vapor from the absorbent garment, increasing the garment comfort and reducing skin rashes and other irritations that result when water vapor is trapped inside the garment and heated by the wearer's body. Many of today's absorbent garments are highly breathable, for maximum wearer comfort.

One shortcoming of breathable absorbent articles is a cold, damp, clammy feel that often occurs on the outside of the garment, i.e., on the outside of the outer cover material. As liquid water in the absorbent core evaporates and passes through the outer cover material, the associated evaporative cooling causes a lowering of temperature of the absorbent core and adjacent outer cover material, resulting in a clammy, damp-feeling outer cover. There is thus a need or desire in the absorbent garment industry for absorbent articles which are highly breathable, yet which reduce or avoid the perceived dampness caused by evaporative cooling, while maintaining low levels of skin hydration.

SUMMARY OF THE INVENTION

The present invention is directed to an absorbent article having a breathable outer cover material and reduced perceived outer cover dampness. The absorbent article includes at least a liquid-permeable top layer, a breathable, substantially liquid impermeable outer cover material, and an absorbent core layer between the top layer and the outer cover material. In accordance with the invention, a low to moderately breathable laminate, including at least a low to moderately breathable film and a nonwoven filament web, is interposed between the absorbent core and the breathable outer cover material. This inner breathable laminate has a breathability which is lower (i.e., lower water vapor transmission rate) than the breathable outer cover material. Preferably, the inner laminate is placed with its film layer facing the absorbent core, and with its nonwoven web layer facing the outer cover material.

The presence of the low to moderately breathable inner laminate reduces perceived dampness of the exposed surface of the outer cover material without significantly reducing moisture flux through the diaper in use, thus maintaining skin health. The film of the inner laminate acts to partially reduce the flux out of the diaper arising from moisture leaving the absorbent core. At the same time, pathways for moisture to leave the skin are maintained, including pathways leading from the skin, around the absorbent core, through an air gap provided by the nonwoven web of the inner laminate, and out the breathable outer cover. The moisture transfer from the skin to the outer cover is actually enhanced, since there is less competition between moisture in the core and moisture in the skin to leave the diaper. In other words, since less moisture in the core is transferred to the air gap provided by the nonwoven web, that air gap is drier; thus, there is a stronger concentration gradient from the air adjacent to the skin, where the humidity is high, to the air gap, where the humidity is lower. This results in increased (ordinary) diffusion of water molecules from the skin to the air gap. Similarly, convective forces caused by movement such as a baby's breathing would also drive moisture away from the skin and into the air gap with an additive result. The drier air gap provides better insulation, causing further reduction in the perceived dampness or clamminess.

With the foregoing in mind, it is a feature and advantage of the invention to provide an absorbent article having a relatively highly breathable outer cover layer and a low or moderately breathable inner laminate which, in combination, after being subjected to a liquid insult, exhibit reduced moisture transfer from the absorbent core through the breathable outercover, thus reducing total moisture flux out of the absorbent article compared to prior art absorbent articles.

It is a further feature and advantage of the invention to maintain pathways for moisture transfer away from the skin, wherein skin hydration levels remain low, possibly lower than conventional highly breathable diapers.

It is also a feature and advantage of the invention to provide a drier air gap between the absorbent core and outer cover, resulting in better insulation and a reduction in perceived outer cover dampness.

It is also a feature and advantage of the invention to provide diapers, child training pants, adult incontinence garments, swim wear, and other (e.g. medical) absorbent products which embody the features of the improved absorbent article of the invention.

The foregoing and other features and advantages will become further apparent from the following detailed description of the preferred embodiments, read in conjunction with the drawings. The detailed description and drawings are intended to be illustrative rather than limiting, the scope of the invention being defined by the appended claims and equivalents thereof.

DEFINITIONS

The terms "breathable film," "breathable laminate" or "breathable outer cover material" refer to a film, laminate, or outer cover material having a water vapor transmission rate ("WVTR") of at least about 300 grams/m$^2$-24 hours, using the WVTR Test Procedure described herein. Terms such as "10% greater breathability" mean, in a relative sense, that a second material has a WVTR which is 10% higher than the WVTR of a first material. The term "higher breathability" simply means that a second material has a higher WVTR than a first material. Breathable materials typically rely on molecular diffusion of vapor, and are substantially liquid impermeable.

The term "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. Pulp or cellulose-based webs are also nonwoven. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers typically having an average fiber denier of about 0.005–10, preferably about 0.05–6, more preferably, about 1–4. Fiber denier is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

The term "film" refers to a thermoplastic film made using a film extrusion process, such as a cast film or blown film extrusion process. The term "water-permeable porous films" refers to films rendered porous by puncturing or aperturing, and to films rendered porous by mixing polymer with filler, forming a film from the mixture, and stretching the film.

The term "foam material" refers to a thermoplastic layer material made with the aid of a foaming process. The term "open-celled foam material" refers to a foam layer whose cells interconnect, or otherwise create pores from one surface of the layer to the opposite surface.

The term "polymer" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "pulp fibers" refers to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

The term "superabsorbent material" refers to a water-swellable, water-insoluble organic or inorganic material capable, under the most favorable conditions, of absorbing at least about 20 times its weight, preferably at least about 30 times its weight in an aqueous solution containing 0.9% by weight sodium chloride.

The term "personal care absorbent product" includes without limitation diapers, training pants, swim wear, absorbent underpants, baby wipes, adult incontinence products, and feminine hygiene products.

The term "medical absorbent product" includes without limitation absorbent garments, underpads, bandages, absorbent drapes, and medical wipes.

Detailed Description of the Presently Preferred Embodiments

Figure 1:
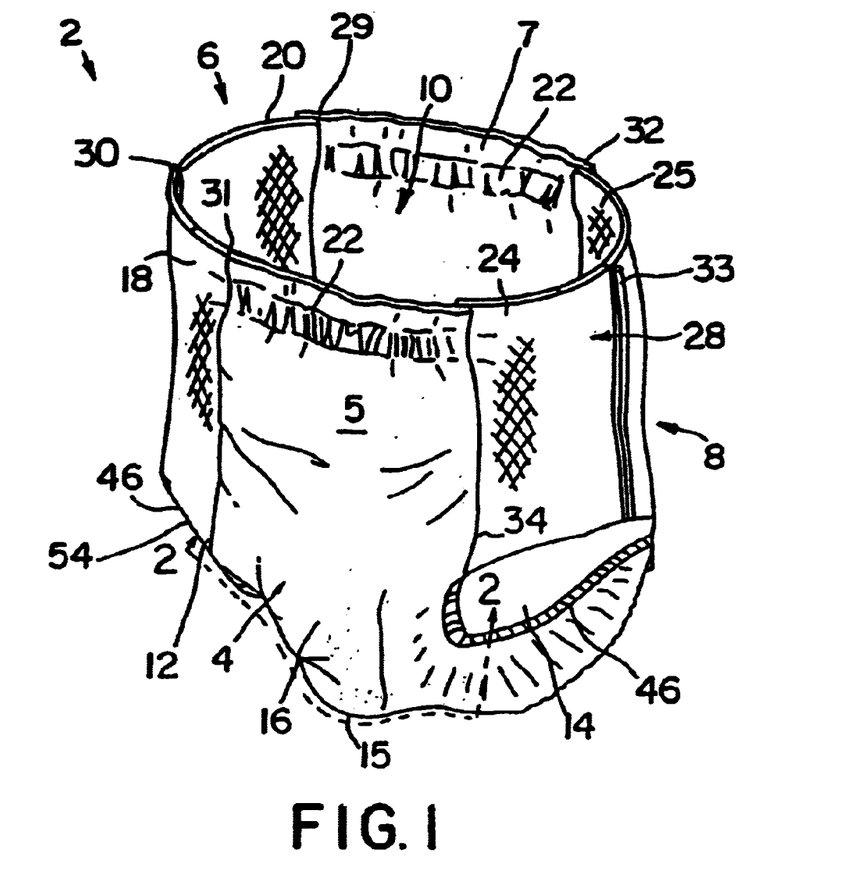
FIG. 1 is a perspective view of an absorbent article of the invention.

Referring to FIG. 1 of the drawings, an absorbent garment 2 of the invention has a pant-like configuration useful for diapers, child training pants, child swim wear, adult incontinence articles, and the like. The garment 2 includes a waste containment section ("chassis") 4 having a front portion 5 and a rear portion 7 joined by a central ("crotch") portion 15, and two side portions 6 and 8, each of which is connected at its edges to the front and rear portions. The side portion 6 includes stretchable panels 18 and 20 joined to each other along seam 30, and joined to the waste containment section along seams 29 and 31. Each of the seams 29, 30 and 31 is longitudinally oriented, and extends from the top of the waist opening 10 to a leg opening 12. The side portion 8 includes stretchable panels 24 and 26 joined to each other along seam 33, and joined to the waste containment section along seams 32 and 34. Each of the seams 32, 33 and 34 is longitudinally oriented, and extends from the top of the waist opening to a leg opening 14.

The chassis 4 includes multiple layers (described below) including, for instance, a liquid-permeable top layer 21, an absorbent core layer 17, and a relatively more breathable liquid-impermeable outer cover layer 16 which faces away from the wearer. A low to moderately breathable inner laminate 50, positioned between the absorbent core 17 and outer cover 16, is described below. The waste containment section 4 also includes elasticized waist portions 22 on the front and back of the garment. The leg opening portions 12 and 14 also include elastic portions 46 which extend substantially around the portion of the leg openings defined by the waste containment section 4.

Figure 2:
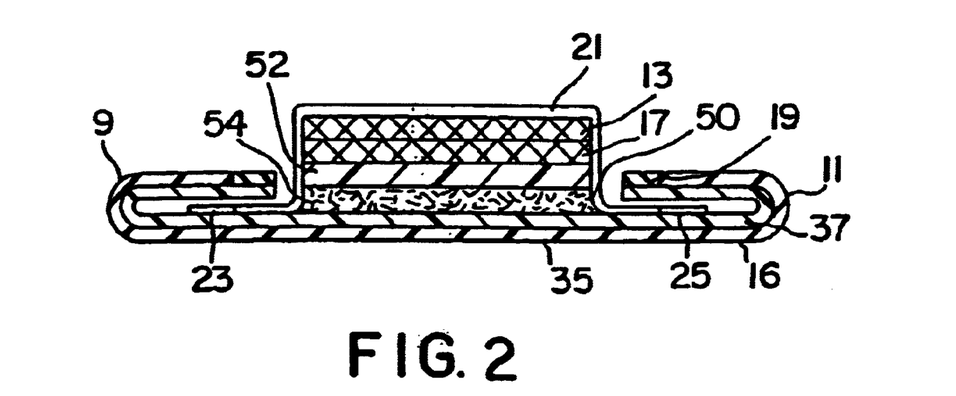
FIG. 2 is an expanded cutout view of an absorbent article of the invention, taken along the line 2—2 in FIG. 1.

FIG. 2 shows an expanded cutout view of the individual layers of the absorbent article, taken along line 2—2 in FIG. 1. Referring to FIG. 2, the absorbent garment 2 includes several layers in the central region 15. The layers include a liquid-permeable top layer 21, a liquid-permeable surge layer 13 adjacent and below the top layer 21, an absorbent core layer 17 adjacent and below the surge layer 13, a low to moderately breathable inner laminate 50 adjacent and below the absorbent core layer 17, and a more breathable, substantially liquid impermeable outer cover 16 adjacent and below the inner breathable laminate 50.

In the embodiment shown, the top layer 21 and outer cover material 16 are wider than surge layer 13, absorbent core 17, and inner laminate 50. The top layer 21 substantially surrounds the surge layer 13, absorbent core 17, and inner laminate 50, and is affixed at end regions 23 and 25 to the outer cover material 16 using an adhesive, ultrasonic or thermal bonding technique. The outer cover material 16 is folded over at both lateral ends 9 and 11, so that it overlaps and envelops the edges 23 and 25 of the top layer 21. Within the overlap, the layers can be bonded together using thermal, ultrasonic, or adhesive bonding. The elastic regions 46 can be formed with elastic bands 19 affixed to, and/or within, the outer cover material 16 using an adhesive, ultrasonic, or thermal bonding technique.

The longitudinal seams 29–34 may be formed by conventional methods including, without limitation, ultrasonic welding, thermal bonding, adhesive bonding, stitch bonding and the like. Ultrasonic welding is a presently preferred technique. The various bonding techniques are conventional, and are neither critical nor limiting as to the present invention.

The stretchable side panels 6 and 8 can be constructed of conventional woven or nonwoven materials, formed from a wide variety of elastic and stretchable polymers. The terms "elastic" and "stretchable" include any material which can be stretched, and which tends to return to its original shape when relaxed. Suitable polymers include without limitation block copolymers of polystyrene, polyisoprene and polybutadiene; copolymers of ethylene, natural rubbers and urethanes; and combinations of the foregoing. Particularly suitable are styrene-butadiene block copolymers sold by Shell Chemical Co. under the trade name KRATON®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels. The stretchable side panels are preferably rectangular in shape, and preferably extend from the top of the waist opening 10 to the leg openings 12 and 14. The side panels may also be laminates of multiple layers, and are preferably breathable to water vapor but impervious to liquids.

Both the surge layer 13 and body side liner 21 are constructed from highly liquid pervious materials. These layers function to transfer liquid from the wearer to the absorbent layer 17. Suitable materials include porous woven materials, porous nonwoven materials, and apertured films. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. Either layer may also be an apertured plastic film. The various layers of the garment 2 have dimensions which vary depending on the size and shape of the wearer.

The absorbent layer 17 can be made of wood pulp fluff or a mixture of wood pulp fluff and a superabsorbent material, or a wood pulp fluff integrated with a thermoplastic absorbent material treated with a surfactant. Thermal binders, such as Pulpex®, can be used in blends or layering with the fluff and superabsorbent. The absorbent layer 17 can also be a batt of meltblown synthetic fibers, a bonded carded web of synthetic or natural fibers or blends thereof, a composite of meltblown fibers and the like. The synthetic fibers can be, but are not limited to, polypropylene, polyethylene, polyester and copolymers of these or other polyolefins.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

The inner laminate material 50 is breathable to water vapor. Generally the inner laminate 50 will have a WVTR of at least about 300 grams/m$^2$-24 hours using the test procedure described below, preferably in a range of about 1000 to about 5000 grams/m$^2$-24 hours, more preferably in a range of about 1500 to about 4000 grams/m$^2$-24 hours. The outer cover 16 is also breathable to water vapor, and has breathability higher than the inner laminate 50. For instance, if the inner laminate 50 has a WVTR of 1000 grams/m$^2$-24 hours, then the outer cover 16 should have a WVTR of at least about 1001 grams/m$^2$-24 hours. Preferably, the outer cover 16 should be at least about 5% more breathable than the inner laminate 50, as expressed in terms of WVTR. More preferably, the outer cover 16 is at least about 10% more breathable, and most preferably at least about 20% more breathable than the inner laminate 50. By and large, the WVTR's of the laminates correspond to the WVTR's of the breathable film components of the laminates. The nonwoven web structures are more open, and have little impact on the overall WVTR's as long as interfilament bonding does not occupy more than about 25% of the planar area of the nonwoven web.

The outer cover 16 can be made from one or more woven or nonwoven materials, films, or a breathable microporous film laminated to a nonwoven material, including, for instance, cast or blown films of polyethylene, polypropylene, polyester or blends thereof mixed with a particulate filler and stretched to cause breathability. The outer cover 16 may also be a composite of a bonded carded or spunbonded or meltblown material, for example, a spunbonded-meltblown composite of thermoplastic material or a spunbonded-meltblown-spunbonded thermoplastic material, wherein the spunbonded layer can provide a cloth-like texture and the meltblown layer can provide liquid impermeability. Materials of which the outer cover 16 can be made include nonwovens having a high basis weight, such as about 0.4 ounces per square yard, or greater.

The outer cover 16 preferably includes extruded films of polyolefin polymers or copolymers, or other thermoplastic materials mixed with a filler and stretched to cause breathability. Generally the outer cover 16 will have a length from about 12 inches to about 30 inches, and a width from about 3 inches to about 20 inches, depending on the wearer's size. In the embodiment shown in FIG. 2, the outer cover 16 may include a woven or nonwoven cloth outer layer 35 and liquid-impervious breathable film inner layer 37, joined by thermal or ultrasonic bonding, or an adhesive. For instance, the layer 35 may be a polypropylene spunbond web. The layer 37 may be a breathable microporous film prepared by stretch-thinning a film formed from a blend of one or more polyolefins, and an inorganic particulate filler.

Figure 3:
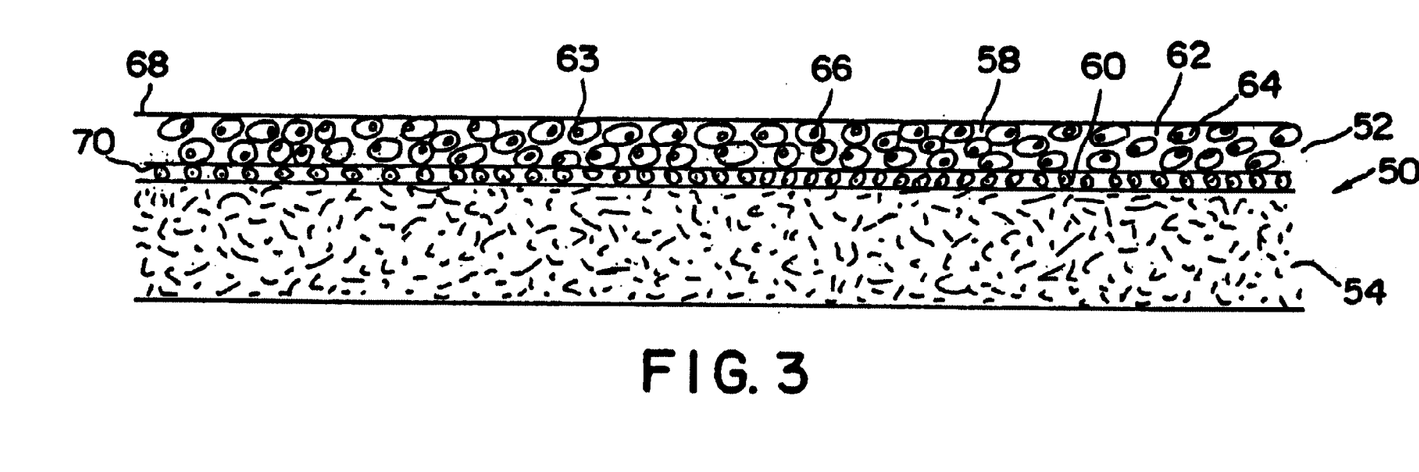
FIG. 3 illustrates one embodiment of an inner laminate used in the absorbent article of the invention.

FIG. 3 illustrates one embodiment of an inner laminate 50 used in the invention. In accordance with the invention, the inner laminate 50 is positioned between the outer cover 16 and the absorbent layer 17. The inner laminate 50 includes a breathable film 52 and a nonwoven filament layer 54. Preferably, the inner laminate 50 is positioned so that the breathable film 52 faces toward the absorbent layer 17, and the nonwoven filament layer 54 faces toward the outer cover 16 (e.g., toward the breathable film component 37 of the outer cover 16 in FIG. 2).

The breathable film component 52 includes at least one microporous layer 58. The microporous layer 58 can be formed using a variety of known technologies. Preferably, the microporous layer 58 includes a polymer matrix 62, a plurality of voids 64 within the matrix surrounded by relatively thin microporous membranes 63 defining tortuous paths, and one or more filler particles 66 in each void 64. The layer 58 is microporous and breathable, wherein the microporous membranes 63 between the voids readily permit molecular diffusion of water vapor from a first surface 68 to a second surface 70 of the film layer 58.

The polymer matrix 62 can be formed from any suitable film-forming thermoplastic polymer. Examples of suitable polymers include without limitation polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain. Other suitable matrix polymers include without limitation elastomers, for example polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly (ethylene-butylene)/polystyrene, poly (styrene/ethylene-butylene/styrene), and the like. Metallocene-catalyzed polyolefins are also useful, including those described in U.S. Pat. Nos. 5,571,619; 5,322,728; and 5,272,236, the disclosures of which are incorporated herein by reference.

Polymers made using metallocene catalysts have a very narrow molecular weight range. Polydispersity numbers (Mw/Mn) of below 4 and even below 2 are possible for metallocene-produced polymers. These polymers also have a controlled short chain branching distribution compared to otherwise similar Ziegler-Natta produced type polymers. It is also possible using a metallocene catalyst system to control the isotacticity of the polymer quite closely.

The filler particles 66 can include any suitable inorganic or organic filler. The filler particles 66 are preferably small, in order to maximize vapor transmission through the voids. Generally, the filler particles should have a mean particle diameter of about 0.1–7.0 microns, preferably about 0.5–5.0 microns, most preferably about 0.8–2.0 microns. Suitable fillers include without limitation calcium carbonate, non-swellable clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles. Calcium carbonate is a presently preferred filler. Linear low density polyethylene (Ziegler-Natta or metallocene-catalyzed, or a blend thereof) is a presently preferred polymer matrix material.

The filler particles 66 may be coated with a minor quantity (e.g. up to 2% by weight) of a fatty acid or other material to ease their dispersion in the polymer matrix. Suitable fatty acids include without limitation stearic acid, or a larger chain fatty acid such as behenic acid. The amount of filler particles 66 in the layer 52 should range from about 30–80% by weight of the layer 58, preferably about 40–70% by weight, most preferably about 50–65% by weight. Similarly, the polymer matrix 62 should constitute about 20–70% by weight of the layer 58, preferably about 30–60% by weight, more preferably about 35–50% by weight.

The polymer composition, filler content, filler particle size and degree of stretching are factors which help determine the breathability of the microporous film layer 58. Generally, the microporous film layer 58 will be less than about 50 microns thick, preferably less than about 30 microns thick, most preferably less than about 20 microns thick. The breathable film 52 may be uniaxially stretched to about 1.1–7.0 times its original length, preferably to about 1.5–6.0 times its original length, most preferably to about 2.5–5.0 times its original length. The film may alternatively be biaxially stretched using conventional techniques familiar to persons skilled in the art.

In the embodiment of FIG. 3, the microporous breathable film layer 58 is adjacent one or two relatively thin outer skin layers 60, in a two or three-layer film 52. The inclusion of one or two skin layers improves film processability and can also contribute heat seal properties to the breathable film 52. The breathable film 52 can be prepared by cast or blown film coextrusion of the layers, by extrusion coating, or by any conventional layering process. The polymers in the outer layer 60 can be the same or different than the polymers in the microporous layer 58. Preferably, the polymers in the outer layer or layers have a lower softening point than in the microporous layer 58, and contribute to the heat sealability of the film 52. To facilitate breathability, the skin layer 60 may contain a particulate filler in substantially the same amount as the microporous base layer 58, and the skin layer 60 may be microporous as well.

Also, the thickness and composition of the outer layer 60 should be selected so as not to substantially impair the moisture transmission through the breathable film 52. This way, the microporous layer 58 may determine the breathability of the entire film. To this end, the skin layer 60 is generally less than about 10 microns thick, preferably less than about 5 microns thick, and preferably constitutes about 10–25% of the entire film thickness. Preferred skin layer polymers include amorphous metallocene or Ziegler Natta-catalyzed elastomeric copolymers of ethylene with a $C_3$–$C_{20}$ alpha-olefin comonomer, having a density less than about 0.89 grams/cc. Also suitable are amorphous poly alpha-olefin (APAO) polymers which can be random copolymers or terpolymers of ethylene, propylene, and butene, and other substantially amorphous or semi-crystalline propylene-ethylene polymers. Also included are ethylene vinyl acetates, propylene vinyl acetates, ethylene methyl acrylates, and blends of any of the foregoing polymers.

The nonwoven web 54 may be a spunbond web, a meltblown web, a bonded carded web, an air laid web, a cellulose or pulp web, or any other fibrous nonwoven or woven web. Preferably, the nonwoven web 54 is made of thermoplastic polymer fibers. The polymers used to make the nonwoven web include the polymers listed above for the breathable microporous film 52, as well as polyamides and polyesters. The nonwoven web 54 is preferably constructed of a polyolefin, more preferably a polyethylene or polypropylene homopolymer or copolymer. The nonwoven web 54 should have a basis weight of about 0.1–4.0 ounces per square yard (osy), preferably about 0.3–2.0 osy, more preferably about 0.4–1.0 osy. The nonwoven web 54 may also be a laminate of more than one nonwoven web layer. For example, web 54 may be a spunbond-meltblown-spunbond structure as disclosed in U.S. Pat. No. 4,041,203, issued to Brock et al. Typically, the web 54 has a high enough breathability so as not to impede the moisture vapor which passes through film 52. Thus, web 54 typically has an open structure.

The nonwoven web 54 and breathable film 52 may be bonded together using thermal calender bonding, ultrasonic bonding, adhesive bonding, or any other suitable bonding technique to make breathable laminate 54. In order to maintain low to moderately high breathability, web 54 and film 52 should not be bonded in such a way that the breathability of the laminate is completely impeded. Preferably, the bonding regions between web 54 and film 52 will cover less than about 30% of the interface between them, more preferably less than about 20% of the interface between them.

In one preferred embodiment, the inner laminate 50 and outer cover 16 both include multilayer film components bonded to a nonwoven web. For instance, the inner laminate 50 and outer cover 16 may each include a two-layer breathable film 52 as described above.

The elastic bands 19 may be in the form of single or multiple bands per leg. A wide variety of elastic materials may be employed. Examples include a film or meltblown web formed using block or graft copolymers of butadiene, isoprene, styrene, ethylene-methyl acrylate, ethylene-vinyl acetate, ethylene-ethyl acrylate or blends thereof. One preferred elastomer is a block copolymer of styrene-ethylbutadiene-styrene. Specific materials of which elastic bands 19 can be made are the Kraton G series from Shell Chemical Company, such as Kraton G-1650, Kraton G-1652, Kraton GX-1657 and preferably Kraton G-2740X. Also, the Kraton D series can be used, as well as polyester elastomeric materials, polyurethane elastomeric materials and polyamide elastomeric materials. Elastomeric single-site or metallocene-catalyzed olefin polymers and copolymers can also be employed. Also, elastic bands 19 can be made of an activatable material applied in an unstretched condition, and activated by heat, light or moisture or radiation to cause shrinkage and elasticity. Activatable elastic materials can be obtained from the 3M Company.

During use, the inner laminate 50 is believed to operate in the following manner to reduce perceived dampness on the external surface of outer cover 16. The film component 52 of inner laminate 50, facing the absorbent core 17, acts as a liquid barrier which helps keep the nonwoven web component 54 of inner laminate 50 (and the air surrounding it) dry. Nonwoven web 54 has air space between its filaments and serves as an air-filled thermal insulation layer between absorbent core 17 and outer cover 16. The less water vapor or liquid in this thermal insulation layer, the lower its thermal conductivity. This thermal insulative layer prevents much of the heat from the hand from reaching the cooled absorbent core, which acts as a heat sink. As a result, the external surface of outer cover 16 is perceived to be drier and warmer to the touch, and the cold, clammy feel is substantially reduced. By designing the inner laminate 50 with lower breathability than the outer cover 16, the perception of outer cover dampness is kept in check. Put another way, the construction and breathability of the outer cover dictates the construction and breathability of the inner laminate, so that the outer cover and inner laminate work together as a system to provide acceptable levels of dampness perception, while maximizing skin health by allowing moisture near the skin to exit the diaper.

The film 52 can be placed between the nonwoven web 54 and the absorbent core 17. The film 52 acts to reduce the flux out of the diaper arising from moisture leaving the absorbent core 17. If the film 52 is breathable, it only partially reduces the flux out of the diaper arising from moisture leaving the absorbent core 17. Regardless of the breathability of the film 52, direct pathways for moisture to leave the skin are maintained. These pathways travel from out of the skin, around the absorbent core 17, through an air gap provided by the nonwoven web 54, and out the breathable outer cover 16. Not only is this moisture transfer from the skin to the outer cover 16 maintained, it is enhanced, since there is less competition between moisture in the absorbent core 17 and moisture in the skin to leave the diaper. In other words, since less moisture in the absorbent core 17 is transferred to the air gap provided by the nonwoven web 54, that air gap is drier; thus, there is a stronger concentration gradient from the air adjacent to the skin, where humidity is high, to the air gap, where humidity is lower. This results in increased (ordinary) diffusion of water molecules from the skin to the air gap along the aforementioned pathway. Similarly, convective forces caused by movement, such as a baby breathing, would also drive moisture away from the skin and into the air gap with an additive result.

Figure 4:
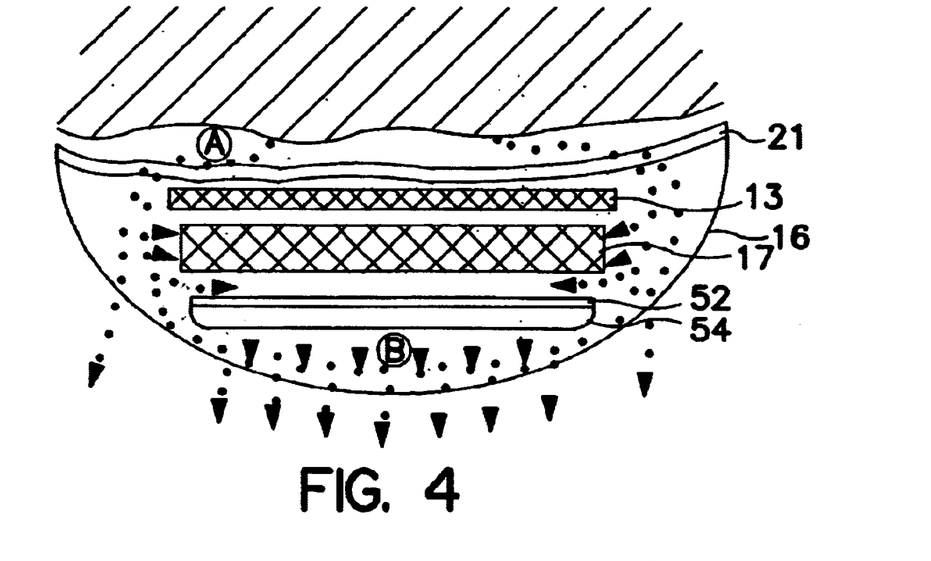
FIG. 4 is a cutout cross-sectional view of an absorbent article of the invention, taken perpendicular to line 2—2 of FIG. 1, illustrating pathways for moisture to leave the skin.

FIG. 4 shows the placement of the film 52 between the nonwoven web 54 and the absorbent core 17. The pathways for moisture to leave the skin are shown in FIG. 4 by dotted pathways. Some of the moisture diffuses through the breathable film 52, and some travels around the absorbent core 17. Point A indicates the high humidity area adjacent to the skin and point B indicates the lower humidity area in the air gap. As explained, there is increased diffusion of water molecules from the skin to the air gap along the pathway illustrated by the dotted line in FIG. 4, which travels around the absorbent core.

Figure 5:
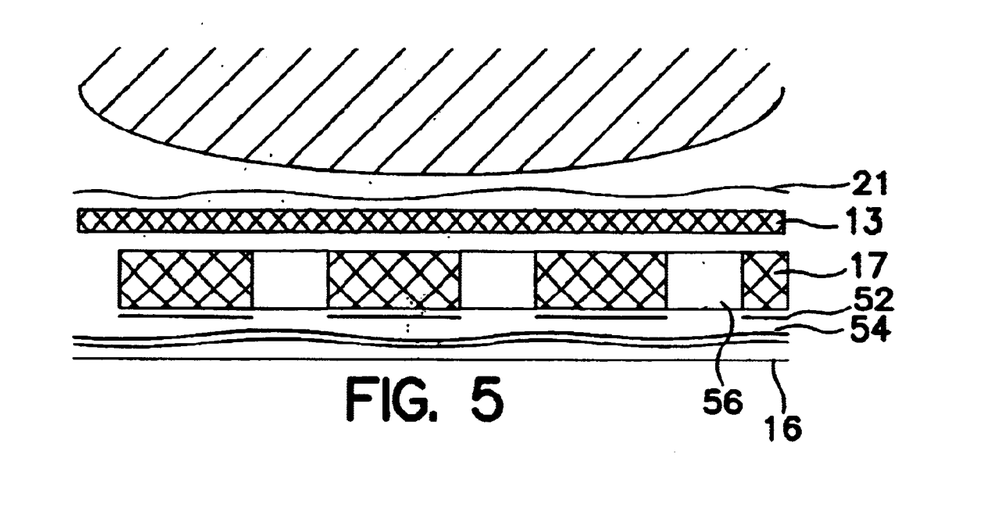
FIG. 5 is a cutout cross-sectional view of an absorbent article of the invention, illustrating an apertured absorbent layer.

In an alternate embodiment shown in FIG. 5, the absorbent layer 17 is apertured, which greatly increases the number of pathways for moisture to leave the skin. To prevent urine from entering the air gap provided by the nonwoven web 54, the film 52 covers the entire inner surface of the nonwoven web 54. The film 52 is breathable at the apertures 56, and is either breathable, less breathable, or non-breathable in the areas adjacent to the absorbent layer 17. Furthermore, the film 52 can have pores that seal when wet. In the embodiment of FIG. 5, the apertures 56 extend through absorbent layer 17 and film 52. In another, similar embodiment, film 52 need not be apertured, and need only be breathable.

Figure 6:
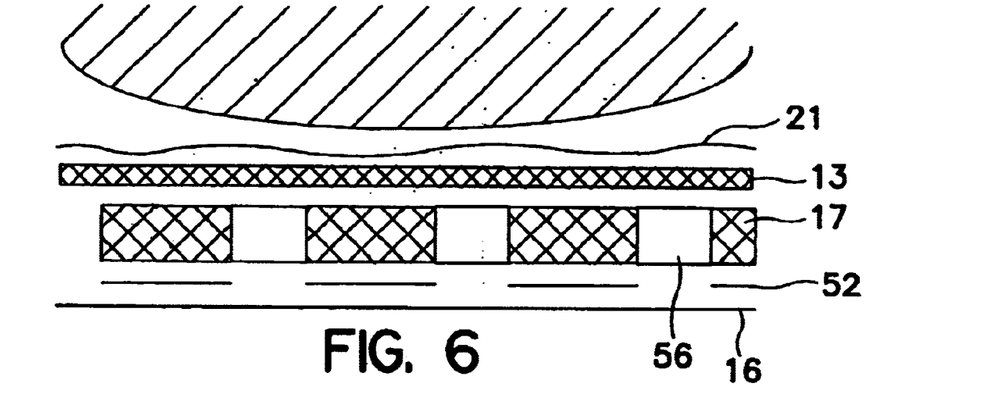
FIG. 6 is a cutout cross-sectional view of an absorbent article of the invention, wherein no nonwoven web is present and a film is apertured with an absorbent layer.

In yet another embodiment of the invention, the nonwoven web 54 is removed altogether. The film 52 and the absorbent layer 17 are apertured together. The film 52 is either non-breathable, or less breathable than the outer cover 16. The nonwoven web 54 is deemed less necessary, since so little fluid is leaving the absorbent layer 17 in a region adjacent to the outer cover. There is minimal evaporative cooling there, so that the outer cover 16 feels less clammy. FIG. 6 shows an embodiment of the invention wherein the nonwoven web 54 is not present and the film 52 is apertured with the absorbent layer 17.

Figure 7:
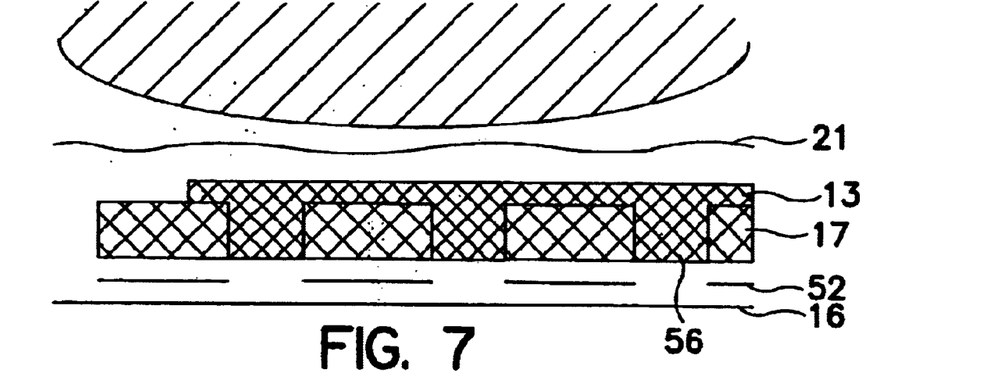
FIG. 7 is a cutout cross-sectional view of an absorbent article of the invention, wherein a surge layer extends to fill the apertures in an apertured absorbent layer.

In a further embodiment of the invention, the surge layer 13 extends to fill the apertures 56 in the absorbent layer 17, to maximize surge capacity while minimizing pooling on the skin surface. FIG. 7 shows an embodiment of the invention wherein the surge layer 13 extends to fill the apertures 56 in the absorbent layer 17.

In still another embodiment of the invention, with reference to FIG. 3, a plurality of odor-sorbing and/or moisture-sorbing particles may be incorporated into the inner laminate 52, particularly within the nonwoven web component 54. Odor-sorbing particles may include activated carbon, zeolites, clay, baking soda, or the like, or a combination of them. Moisture-sorbing particles may include superabsorbent polymers, dessicants and/or humectants. Alternatively or additionally, the fibers in the nonwoven web 54 may be treated with odor and/or moisture-sorbing substances. The odor-absorbing particles or other substance may also absorb moisture. The effect of using these substances is to keep the air within the nonwoven web 54 drier and with reduced odors.

Test Procedure For Water Vapor Transmission Rate (WVTR)

The following procedure is described for testing of the water vapor transmission rate (WVTR) for breathable films and laminates. The WVTR is measured in a manner similar to ASTM Standard Test Method for Water Vapor Transmission of Materials, Designation E-96-80 as follows. For the purposes of the present invention, 3 inch diameter (76 mm) circular samples are cut from the test material and from a control material, CELGUARD®2500 (Hoechst Celanese Corporation). CELGUARD®2500 is a 0.0025 cm thick film composed of microporous polypropylene. Two or three samples are prepared for each material.

The cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred millimeters of distilled water is poured into each Vapometer cup, and each of the individual samples of the test materials and control material are placed across the top area of an individual cup. Screw-on flanges are tightened to form a seal along the edges of the cups leaving the associated test material or control material exposed to the ambient atmosphere over a 62 millimeter diameter circular area (an open, exposed area of about 30 $cm^2$). The cups are then weighed, placed on a tray, and set in a forced air oven set at 100° F. (38° C.).

The oven is a constant temperature oven with external air through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary test WVTR value is calculated as follows:

$$\text{Test } WVTR = [(\text{grams weight loss over 24 hours}) \times 7571] \div 24$$

The relative humidity within the oven is not specifically controlled. Under predetermined set conditions of 100° F. and ambient relative humidity, the WVTR for CELGUARD®2500 has been determined to be 5000 $g/m^2/24$ hours. Accordingly, CELGUARD®2500 is run as a control sample with each test and the resulting values are corrected in accord with the variation of the control relative to its known WVTR.

While the embodiments of the invention described herein are presently considered preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent article, comprising:
   a liquid-permeable top layer;
   an absorbent core layer;
   a breathable outer cover material; and
   an inner laminate including at least a nonwoven web and a breathable film positioned between the absorbent core layer and the breathable outer cover material, and having a WVTR of at least about 300 grams/m$^2$-24 hours;
   the breathable outer cover material having a WVTR higher than the WVTR of the inner laminate;
   the nonwoven web of the inner laminate forming moisture transfer pathways from a body side surface of the article to a garment side surface of the article beneath the absorbent core layer.

2. The absorbent article of claim 1, wherein the outer cover has a WVTR at least about 5% higher than the WVTR of the inner laminate.

3. The absorbent article of claim 1, wherein the outer cover has a WVTR at least about 10% higher than the WVTR of the inner laminate.

4. The absorbent article of claim 1, wherein the outer cover has a WVTR at least about 20% higher than the WVTR of the inner laminate.

5. The absorbent article of claim 1, wherein the inner laminate has a WVTR of at least about 1000 grams/m$^2$-24 hours.

6. The absorbent article of claim 1, wherein the inner laminate has a WVTR of at least about 1500 grams/m$^2$-24 hours.

7. The absorbent article of claim 1, wherein the breathable film of the inner laminate faces the absorbent core layer.

8. The absorbent article of claim 1, wherein the breathable film of the inner laminate comprises a microporous polyolefin-based film, and the nonwoven web of the inner laminate comprises microfibers.

9. The absorbent article of claim 8, wherein the microporous polyolefin-based film comprises a stretch-thinned film prepared from a mixture of polyolefin and a particulate filler.

10. The absorbent article of claim 8, wherein the nonwoven web comprises a spunbond web.

11. The absorbent article of claim 8, wherein the nonwoven web comprises a meltblown web.

12. The absorbent article of claim 8, wherein the nonwoven web comprises a cellulose web.

13. The absorbent article of claim 8, wherein the nonwoven web comprises a spunbond-meltblown-spunbond laminate.

14. The absorbent article of claim 1, wherein the film and web of the inner laminate are thermally bonded together.

15. The absorbent article of claim 1, wherein the film and web of the inner laminate are adhesively bonded together.

16. The absorbent article of claim 1, wherein the film and web of the inner laminate are ultrasonically bonded together.

17. The absorbent article of claim 1, wherein the outer cover comprises a breathable film laminated to a nonwoven web.

18. The absorbent article of claim 17, wherein the breathable film of the outer cover comprises a microporous polyolefin-based film, and the nonwoven web of the outer cover comprises microfibers.

19. The absorbent article of claim 1, wherein the absorbent core layer comprises apertures.

20. The absorbent article of claim 1, wherein the breathable film comprises apertures.

21. The absorbent article of claim 1, further comprising a plurality of moisture-sorbing and/or odor-sorbing particles in the inner laminate.

22. The absorbent article of claim 1, further comprising a moisture and/or odor-sorbing substance in the nonwoven web.

23. An absorbent article, comprising:
   a liquid-permeable top layer;
   an absorbent core layer;
   an inner laminate including at least a first breathable film laminated to a nonwoven filament web, the first breathable film having a WVTR in a range between about 1000 grams/m$^2$-24 hours and about 4000 grams/m$^2$-24 hours; and
   a breathable outer cover including at least a second breathable film laminated to a nonwoven microfibrous web, the second breathable film having a WVTR higher than the WVTR of the first breathable film of the inner laminate;
   wherein the inner laminate is positioned between the absorbent core layer and the breathable outer cover, and the nonwoven filament web of the inner laminate forms moisture transfer pathways from a body side surface of the article to a garment side surface of the article beneath the absorbent core layer.

24. The absorbent article of claim 23, wherein the inner laminate is positioned with the breathable film of the inner laminate facing the absorbent core.

25. The absorbent article of claim 23, wherein the outer cover is positioned with the breathable film of the outer cover facing the inner laminate.

26. The absorbent article of claim 23, wherein the breathable film of the outer cover and the nonwoven web of the inner laminate face each other.

27. An absorbent article, comprising:
   a liquid-permeable top layer;
   an absorbent core layer;
   a breathable inner laminate including at least a breathable film laminated to a nonwoven web, having a WVTR of at least about 300 grams/m$^2$-24 hours; and
   a breathable outer cover including at least a breathable film laminated to a nonwoven web;
   wherein the inner laminate is positioned between the absorbent core and the breathable outer cover, the breathable outer cover has a WVTR higher than the WVTR of the inner laminate, and the nonwoven web of the inner laminate forms moisture transfer pathways from a body side surface of the article to a garment side surface of the article beneath the absorbent core layer.

28. The absorbent article of claim 27, comprising a diaper.

29. The absorbent article of claim 27, comprising a training pant.

30. The absorbent article of claim 27, comprising an adult incontinence garment.

31. The absorbent article of claim 27, comprising swim wear.

32. The absorbent article of claim 27, comprising a medical absorbent product.

33. An absorbent article, comprising:
   a liquid-permeable top layer;
   an apertured absorbent core layer;
   a breathable outer cover material; and an inner laminate including at least a nonwoven web and a film positioned between the absorbent core layer and the breathable outer cover material, and having a WVTR;

the breathable outer cover material having a WVTR higher than the WVTR of the inner laminate;

the nonwoven web of the inner laminate forming moisture transfer pathways from a body side surface of the article to a garment side surface of the article beneath the absorbent core layer.

34. The absorbent article of claim 33 wherein the film entirely covers one side of the nonwoven web.

35. The absorbent article of claim 33 wherein the film comprises pores that seal when wet.

36. The absorbent article of claim 33 wherein the film is breathable at apertures in the absorbent core layer.

37. The absorbent article of claim 33 wherein the film is breathable in areas adjacent to the absorbent core layer.

38. The absorbent article of claim 33 wherein the film is non-breathable in areas adjacent to the absorbent core layer.

39. The absorbent article of claim 36 wherein the film is less breathable in areas adjacent to the absorbent core layer than at the apertures in the absorbent core layer.

40. An absorbent article, comprising:
a liquid-permeable top layer;
an absorbent core layer;
a breathable outer cover material; and
an inner laminate including a film positioned between the absorbent core layer and the breathable outer cover material;
wherein the film and the absorbent core layer are apertured together.

41. The absorbent article of claim 40 wherein the film is less breathable than the outer cover material.

42. The absorbent article of claim 40 wherein the film is non-breathable.

43. The absorbent article of claim 40 further comprising a surge layer positioned between the top layer and the inner laminate, wherein the surge layer extends into apertures in the absorbent core layer.

* * * * *